(12) United States Patent
Buisson

(10) Patent No.: US 9,095,693 B2
(45) Date of Patent: Aug. 4, 2015

(54) CONNECTING DEVICE FOR AN ADMINISTRATION SYSTEM FOR MEDICAL TREATMENT FLUIDS

(71) Applicant: DORAN INTERNATIONAL, Toussieu (FR)

(72) Inventor: Philippe Buisson, Toussieu (FR)

(73) Assignee: DORAN INTERNATIONAL (FR)

( * ) Notice: Subject to any disclaimer, the term of this patent is extended or adjusted under 35 U.S.C. 154(b) by 162 days.

(21) Appl. No.: 13/932,788

(22) Filed: Jul. 1, 2013

(65) Prior Publication Data

US 2014/0296835 A1 Oct. 2, 2014

(30) Foreign Application Priority Data

Apr. 2, 2013 (FR) ...................................... 13 52972

(51) Int. Cl.
*A61M 25/16* (2006.01)
*A61M 25/18* (2006.01)
*A61M 39/00* (2006.01)
*A61M 39/10* (2006.01)
*A61M 39/02* (2006.01)

(52) U.S. Cl.
CPC ..... *A61M 39/105* (2013.01); *A61M 2039/1033* (2013.01); *A61M 2206/11* (2013.01)

(58) Field of Classification Search
CPC .................. A61M 39/105; A61M 2039/1033; A61M 2206/11; A61M 39/10; A61J 1/14
USPC .................................................. 604/533–539
See application file for complete search history.

(56) References Cited

U.S. PATENT DOCUMENTS

| 5,533,996 | A | * | 7/1996 | Murphey et al. | ............... 604/535 |
| 6,780,167 | B2 | | 8/2004 | Leone | |
| 2008/0105318 | A1 | * | 5/2008 | Leone | ............ 137/896 |
| 2010/0318069 | A1 | * | 12/2010 | Hall et al. | ..................... 604/535 |

* cited by examiner

*Primary Examiner* — Rebecca E Eisenberg
(74) *Attorney, Agent, or Firm* — Cantor Colburn LLP

(57) ABSTRACT

A connecting device includes a connecting member having a primary flow channel and secondary flow channels, each provided with a proximal aperture intended to be fluidically connected to a respective tube for medical treatment fluid administration and with a distal aperture, the distal aperture of the primary flow channel being positioned between the distal apertures of the secondary flow channels, and a connection endpiece intended to be connected to a catheter, the connection endpiece having a mounting portion in which the connecting member is mounted, the connecting member and the connection endpiece delimiting an internal chamber into which open the distal apertures of the primary and secondary flow channels, where the cross-section of the distal aperture of the primary flow channel is greater than the cross-section of the proximal aperture of the primary flow channel.

9 Claims, 3 Drawing Sheets

CONNECTING DEVICE FOR AN ADMINISTRATION SYSTEM FOR MEDICAL TREATMENT FLUIDS

TECHNICAL FIELD

The present invention relates to a connection device for a system for administering medical treatment fluids.

BACKGROUND

Document U.S. Pat. No. 6,780,167 discloses a connection device for a system for administering medical treatment fluids, comprising:
  a connection member comprising a primary flow channel and secondary flow channels, each flow channel comprising a proximal aperture intended to be fluidically connected to a respective medical treatment fluid administration tube and a distal aperture, and
  a connection endpiece intended to be connected to a catheter, the connection endpiece comprising a mounting portion in which the connection member is mounted, the connection member and the connection endpiece delimiting an internal chamber into which open the distal apertures of the primary and secondary flow channels, the connection endpiece further comprising an outlet orifice opening into the internal chamber.

During the use of such a connection device, the fluids flowing inside the primary and secondary flow channels mix in the internal chamber before being administered to the patient. Such mixing may be disadvantageous, in particular when the fluids from the different flow channels are incompatible and may precipitate. In fact, mixing of such fluids may lead to unsuitable treatment for the patient.

In order to avoid mixing of the fluids from the primary and secondary flow channels, it is known from document US 2008/0105318 to position the distal aperture of the primary flow channel between the distal apertures of the secondary flow channels, form a guide ribs inside the internal chamber, and configure the internal chamber such that its distal end has a diameter larger than that of its proximal end.

Such a connection device has a complex connection endpiece and requires a specific arrangement of the different flow channels. Furthermore, such a connection device requires a primary flow channel with a large cross-section so as to avoid any mixing of the fluids coming from the secondary flow channels, which requires a significant flow rate of the fluid flowing in the primary flow channel.

BRIEF SUMMARY

The present invention aims to resolve these drawbacks.

The technical problem at the base of the invention in particular comprises providing a connection device for an administration system for medical treatment fluids that has a simple and cost-effective structure, and that ensures a satisfactory administration of different medical treatment fluids to a patient, and therefore satisfactory treatment for that patient.

To that end, the present invention relates to a connection device for an administration system for medical treatment fluids, comprising:
  a connection member comprising a primary flow channel and secondary flow channels, each of the primary and secondary flow channels comprising a proximal aperture intended to be fluidically connected to a respective medical treatment fluid administration tube and a distal aperture, the distal aperture of the primary flow channel being positioned between the distal apertures of the secondary flow channels, and
  a connection endpiece intended to be connected to a catheter, the connection endpiece comprising a mounting portion in which the connection member is mounted, the connection member and the connection endpiece delimiting an internal chamber into which open the distal apertures of the primary and secondary flow channels, the connection endpiece further comprising an outlet orifice opening into the internal chamber,
  characterized in that the cross-section of the distal aperture of the primary flow channel is greater than the cross-section of the proximal aperture of the primary flow channel.

Such a configuration of the primary flow channel, and in particular its distal aperture, makes it possible, when the different primary and secondary flow channels are fluidically connected to medical treatment fluid administration tubes, to generate, in the internal chamber, a flow of fluid capable of keeping the fluids from the secondary flow channels separate as far as the catheter connected to the connection endpiece.

These arrangements make it possible to avoid mixing of incompatible fluids within the connection endpiece and the catheter, and in particular precipitation of those incompatible fluids, and therefore to ensure optimal treatment for the patient.

Furthermore, the configuration of the distal aperture of the primary flow channel makes it possible to limit the flow rate of the fluid flowing through the primary flow channel.

Preferably, the primary flow channel is designed to be connected to an administration tube connected to a container containing a physiological serum.

According to a method according to the invention, the distal aperture of the primary flow channel is conformed so as to extend between the different distal apertures of the secondary flow channels. In other words, for each secondary flow channel, the distal aperture of said secondary flow channel is separated from the distal apertures of the other secondary flow channels by at least one portion of the distal aperture of the primary flow channel.

According to one aspect of the invention, the distal aperture of the primary flow channel extends over at least 70%, and preferably over at least 80%, of the width of the internal chamber.

According to one embodiment of the invention, the connection member comprises an end surface, preferably substantially planar, in which the distal apertures of the primary and secondary flow channels emerge. Preferably, the end surface at least partially delimits the internal chamber.

According to one embodiment of the invention, the connection member has a generally frusto-conical shape.

According to one embodiment of the invention, the connection member includes bearing means arranged to cooperate with the assembly portion of the connection endpiece so as to limit the insertion depth of the connection member in the mounting portion. The bearing means for example include a bearing flange formed at one end of the connection member.

According to one embodiment of the invention, the mounting portion of the connection endpiece is substantially frusto-conical.

According to one aspect of the invention, each secondary flow channel has a constant longitudinal section.

According to one aspect of the invention, the connection endpiece is of the Luer or Luer lock type, and comprises a first frusto-conical connection portion fluidically connected to the outlet orifice.

Preferably, the connection endpiece comprises a second connection portion interiorly threaded and surrounding the first frusto-conical connection portion.

According to a first alternative embodiment of the invention, the second connection portion is mounted rotatably with respect to the first frusto-conical connection portion.

According to a second alternative embodiment of the invention, the second connection portion is secured to the first frusto-conical connection portion.

According to one embodiment of the invention, the outlet orifice extends across from the distal aperture of the primary flow channel.

According to one aspect of the invention, the connection member comprises a plurality of receiving housings into each of which a medical treatment fluid administration tube is intended to be inserted and into each of which opens the proximal aperture of a flow channel. Preferably, the receiving housings have an identical cross-section and are advantageously substantially identical.

According to one embodiment of the invention, each receiving housing emerges at one end of the connection member opposite the connection endpiece.

According to one aspect of the invention, the connection member and the connection endpiece are transparent.

According to one embodiment of the invention, the primary flow channel flares towards the internal chamber.

According to one embodiment of the invention, the receiving housings fluidically connected to the secondary flow channels are distributed, preferably regularly distributed, around the receiving housing fluidically connected to the primary flow channel.

According to one embodiment of the invention, the receiving housings extend substantially parallel to each other. Preferably, the receiving housings extend longitudinally.

According to one embodiment of the invention, the secondary flow channels extend substantially parallel to the receiving housings. Preferably, each secondary flow channel extends along an axis substantially combined with the axis of the respective receiving housing.

According to one embodiment of the invention, each secondary flow channel has a circular transverse section.

According to one embodiment of the invention, the internal chamber is laterally delimited by a smooth side wall, and preferably substantially cylindrical or tapered.

According to one embodiment of the invention, at least one of the receiving housings comprises limiting means capable of limiting the insertion depth of the respective administration tube. The limiting means are preferably formed by a shoulder.

According to one embodiment of the invention, the distal aperture of the primary flow channel has an oblong shape, and the connection member comprises two secondary flow channels whereof the distal apertures emerge on either side of the distal aperture of the primary flow channel.

According to another embodiment of the invention, the connection member comprises four secondary flow channels and the distal aperture of the primary flow channel is in the shape of a cross.

According to still another embodiment of the invention, the connection member comprising three secondary flow channels and the distal aperture of the primary flow channel assumes the shape of a Y.

BRIEF DESCRIPTION OF THE DRAWINGS

In any case, the invention will be well understood using the following description in reference to the appended diagrammatic drawing showing, as non-limiting examples, two embodiments of this connection device.

DETAILED DESCRIPTION

Figure 1:
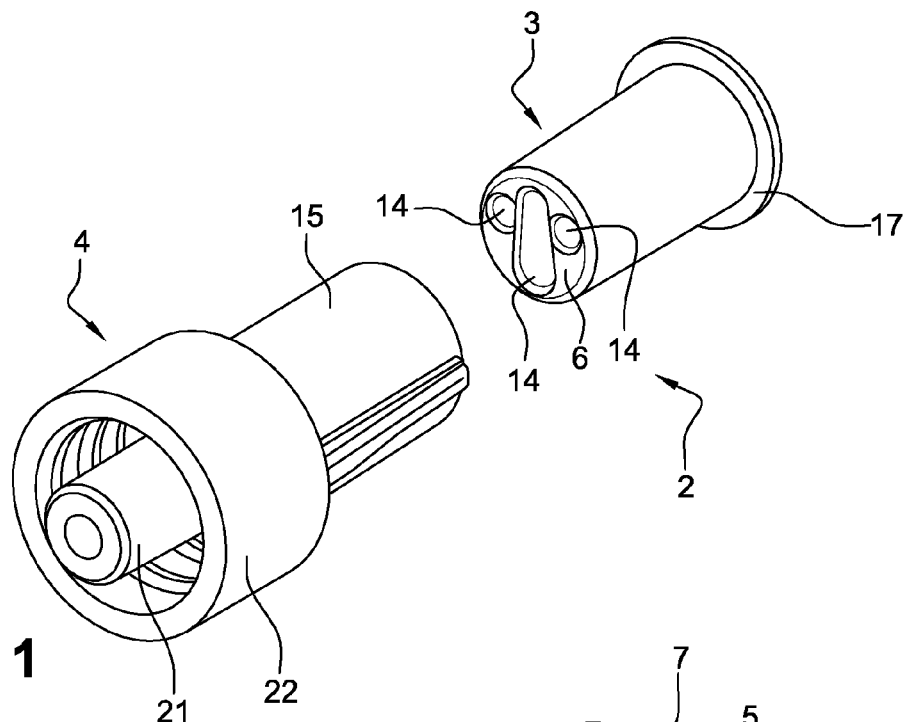
FIG. 1 is an exploded perspective view of a connection device according to a first embodiment of the invention.

FIGS. 1 to 5 show a connection device 2 for an administration system for medical treatment fluids, including a connection member 3 designed to connect administration tubes for medical treatment fluids, and a connection endpiece 4 designed to be connected to a catheter. The connection member 3 and the connection endpiece 4 may for example be made from a transparent plastic material.

The connection member 3 has a generally frusto-conical shape and comprises a first substantially planar end surface 5 across from the connection endpiece 4 and a second substantially planar end surface 6 turned toward the connection endpiece 4.

Figure 2:
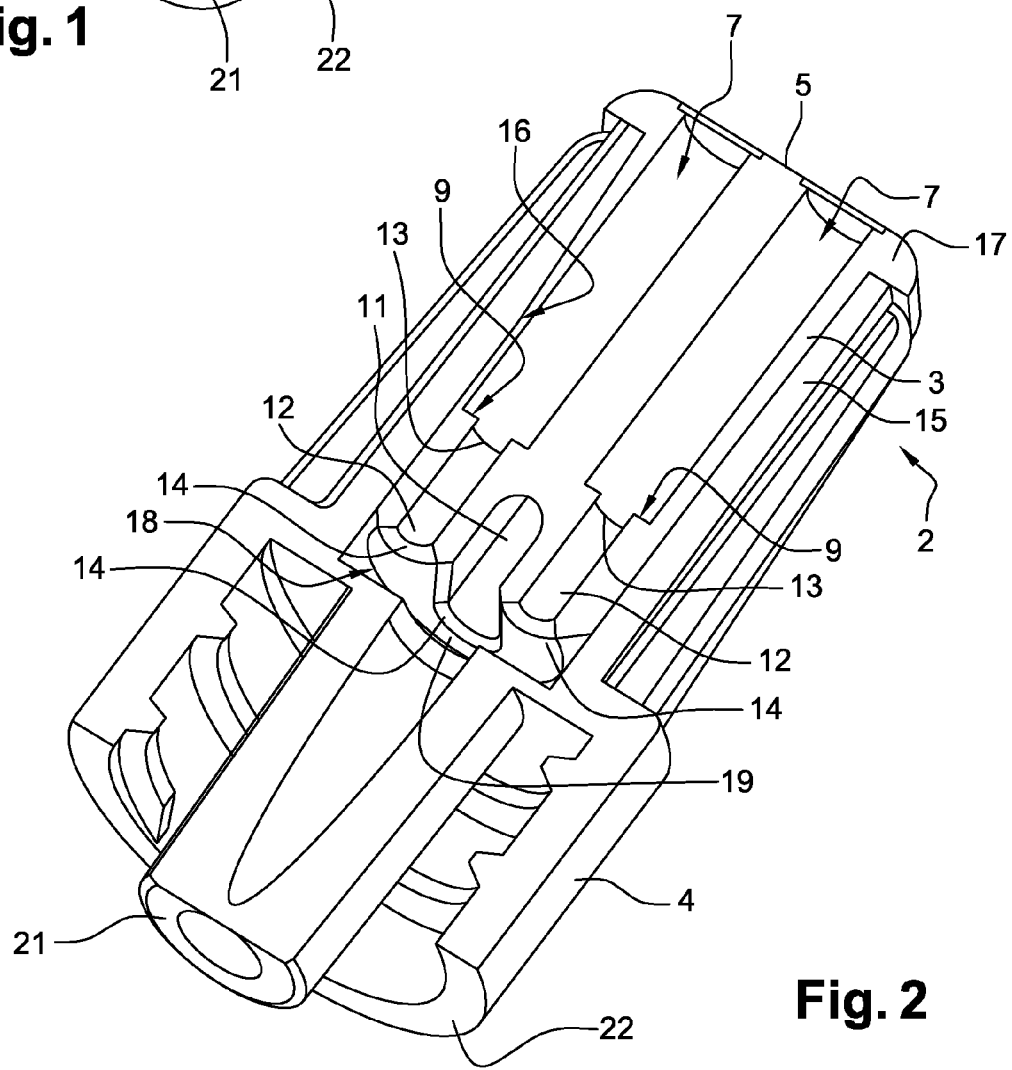
FIGS. 2 and 3 are longitudinal cross-sectional perspective views of the connection device of FIG. 1.
Figure 3:
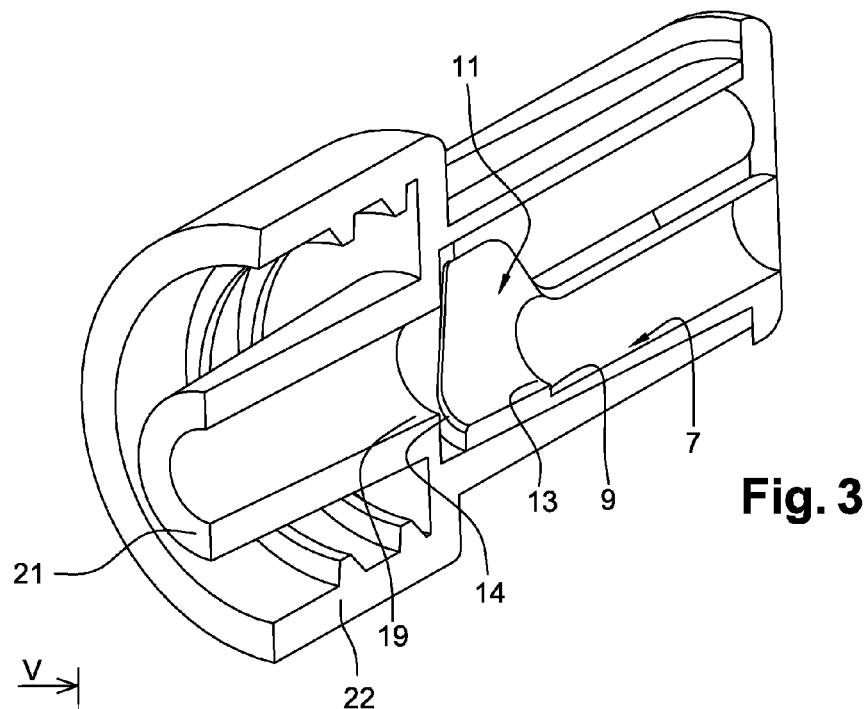
Figure 4:
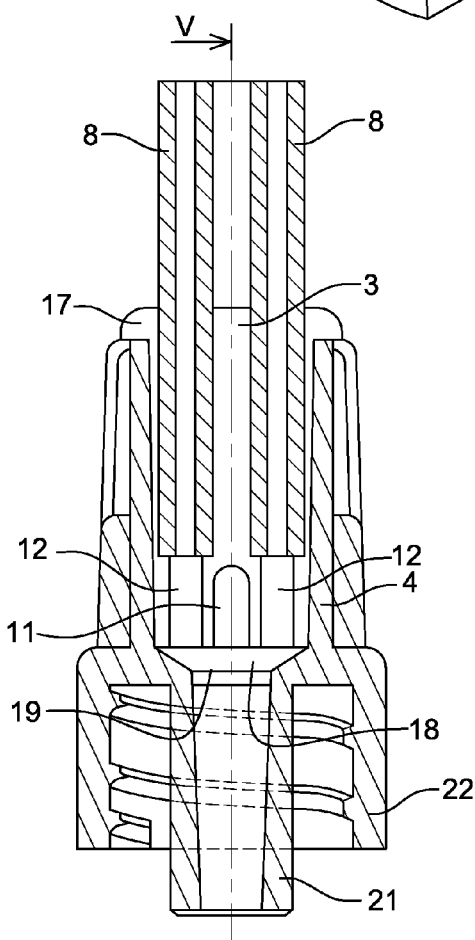
FIG. 4 is a longitudinal cross-sectional view of the connection device of FIG. 1 on which administration tubes are connected.
Figure 5:
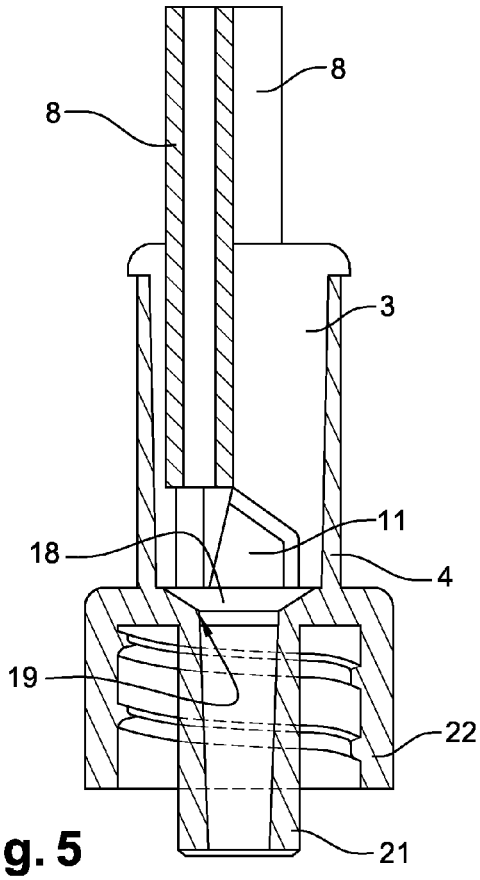
FIG. 5 is a cross-sectional view along line V-V of FIG. 4.

As more particularly shown in FIGS. 2 and 3, the connection member 3 includes a plurality of generally cylindrical receiving housings 7 opening into the first end surface 5 and extending substantially parallel to the longitudinal axis of the connection member 3. Each receiving housing 7 is designed to receive an end portion of a medical treatment fluid administration tube 8. The different administration tubes 8 may for example be independent of one another or may be connected to each other so as to form a set of strippable tubes.

Advantageously, each receiving housing 7 comprises a shoulder 9 capable of limiting the insertion depth of the respective administration tube 8 in said receiving housing.

The connection member 3 further includes a primary flow channel 11 and secondary flow channels 12. Each flow channel 11, 12 comprises a proximal aperture 13 opening into one of the receiving housings 7 and designed to be fluidically connected to the administration tube 8 mounted in said receiving housing, and a distal aperture 14 opposite the proximal aperture 13 and opening into the second end surface 6.

As shown in FIG. 2, the secondary flow channels 12 extend substantially parallel to the receiving housings 7. Preferably, each secondary flow channel 12 extends coaxially to the corresponding receiving housing 7.

Each secondary flow channel 12 for example has a circular transverse section and a constant longitudinal section. The primary flow channel 11 flares toward the second end surface 6. In particular, the transverse section of the distal aperture 14 of the primary flow channel 11 is larger than the transverse section of the proximal aperture 13 of the primary flow channel 11.

In the embodiment shown in FIGS. 1 to 5, the distal aperture 14 of the primary flow channel 11 assumes an oblong shape, and the connection member 3 comprises two secondary flow channels 12 whereof the distal apertures 14 emerge on either side of the distal aperture 14 of the primary flow channel 11.

The connection endpiece 4 comprises a substantially frusto-conical mounting portion 15 delimiting a housing 16 in which the connection member 3 is mounted. Advantageously, the connection member 3 includes a bearing flange 17 formed at the first end surface 5 and arranged to cooperate with the assembly portion 15 of the connection endpiece 4 so as to limit the insertion depth of the connection member 3 into the mounting portion 15.

The connection member 3 and the connection endpiece 4 delimit an internal chamber 18 into which the distal apertures 14 of the primary and secondary flow channels 11, 12 open.

The connection endpiece 4 further comprises an outlet orifice 19 emerging in the internal chamber 18, and situated across from the distal aperture 14 of the primary flow channel 11. Preferably, the distal aperture 14 of the primary flow channel 11 has a length corresponding to at least 70% of the diameter of the internal chamber 18.

In the embodiment shown in FIGS. 1 to 5, the connection endpiece 4 is of the Luer Lock type, and thus comprises a first frusto-conical connection portion 21 fluidically connected to the outlet orifice 19, and a second interiorly threaded connection portion 22 and surrounding the first connection portion 21. The second connection portion 22 is secured to the first connection portion 21. However, according to one alternative embodiment of the invention, the second connection portion 22 could be rotatably mounted with respect to the first connection portion 21. According to still another alternative embodiment of the invention, the connection endpiece 4 could be of the Luer type, and therefore not have the second connection portion.

The method for using the connection device 2 will now be described.

This usage method includes the following steps:
connecting the first and second connection portions 21, 22 to a catheter (not shown in the figures) positioned on a patient to be treated,
inserting the free end portion of a first administration tube 8 into the receiving housing 7 fluidically connected to the primary flow channel 11, the first administration tube 8 being fluidically connected to a first container for example containing physiological serum,
inserting the free end portions of second and third administration tubes 8 respectively into the receiving housings 7 fluidically connected to the secondary flow channels 12, the second and third administration tubes 8 being fluidically connected to second and third containers, respectively, containing different medical treatment fluids, and
causing the fluids contained in the first, second and third containers to flow in the corresponding administration tubes 8.

The configuration of the primary flow channel 11, and more particularly its distal aperture 14, makes it possible to generate, in the internal chamber 18, a flow of fluid capable of keeping the fluids coming from the secondary flow channels 12 separated up to the catheter connected to the connection endpiece 4.

These arrangements make it possible to avoid mixing of the fluids coming from the second and third containers within the connection endpiece 4 and the catheter, and in particular precipitation of those fluids, which may be incompatible, and therefore to ensure optimal treatment for the patient.

Figure 6:
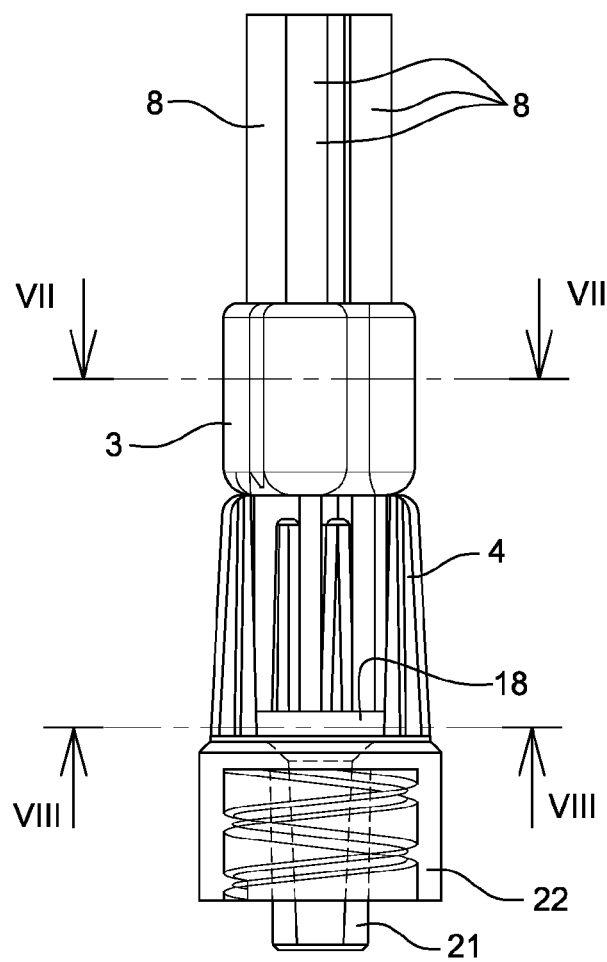
FIG. 6 is a side view of the connection device according to a second embodiment of the invention.
Figure 7:
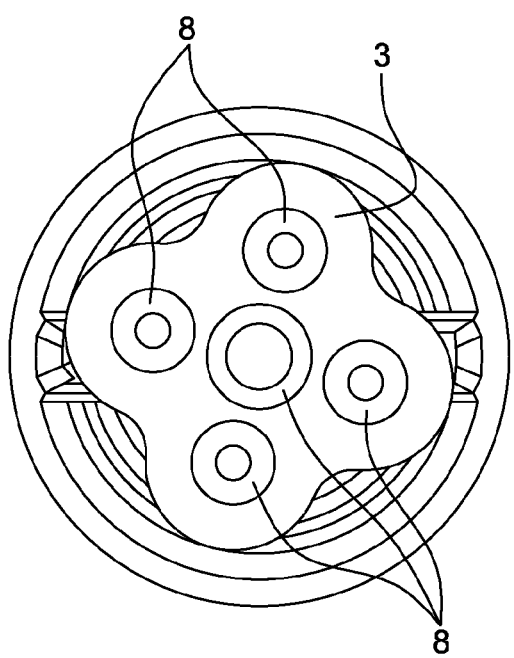
FIG. 7 is a cross-sectional view along line VII-VII of FIG. 6.
Figure 8:
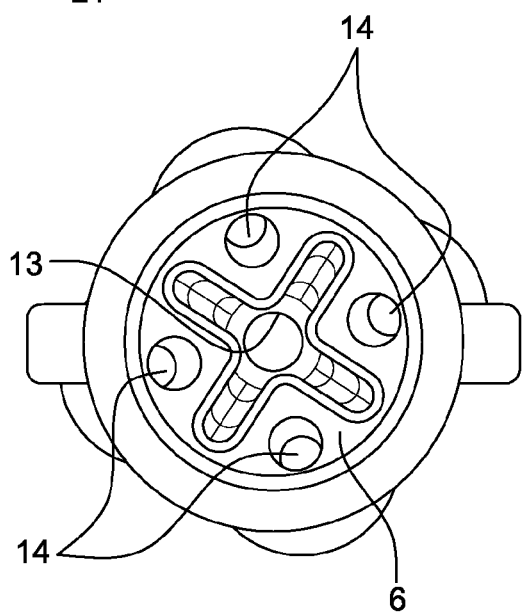
FIG. 8 is a cross-sectional view along line VIII-VIII of FIG. 6.

FIGS. 6 to 8 show a connection device 2 according to a second embodiment that differs from that shown in FIGS. 1 to 5 essentially in that the connection member 3 comprises four secondary flow channels 12 and in that the distal aperture 14 of the primary flow channel 11 is in the shape of a cross.

According to this embodiment, the distal aperture 14 of the primary flow channel 11 is configured so as to extend between the different distal apertures 14 of the secondary flow channels 12. Furthermore, according to this embodiment, the receiving housings 7 fluidically connected to the secondary flow channels 12 are regularly distributed around the receiving housing 7 fluidically connected to the primary flow channel 11.

According to a third embodiment of the invention not shown in the figures, the connection member 3 could comprise three secondary flow channels 12 and the distal aperture 14 of the primary flow channel 11 could assume the shape of a Y.

The invention is of course not limited solely to the embodiments of this connection device described above as examples, but on the contrary encompasses all alternative embodiments.

The invention claimed is:

1. A connecting device for an administration system for medical treatment fluids, including:
   a connecting member comprising a primary flow channel and secondary flow channels, each of the primary and secondary flow channels comprising a proximal aperture intended to be fluidically connected to a respective medical treatment fluid administration tube and a distal aperture, the distal aperture of the primary flow channel being positioned between the distal apertures of the secondary flow channels, and
   a connection endpiece intended to be connected to a catheter, the connection endpiece comprising a mounting portion in which the connecting member is mounted, the connecting member and the connection endpiece delimiting an internal chamber into which open the distal apertures of the primary and secondary flow channels, the connection endpiece further comprising an outlet orifice opening into the internal chamber,
   wherein the cross-section of the distal aperture of the primary flow channel is greater than the cross-section of the proximal aperture of the primary flow channel.

2. The connecting device according to claim 1, wherein the distal aperture of the primary flow channel is conformed so as to extend between the different distal apertures of the secondary flow channels.

3. The connecting device according to claim 1, wherein each secondary flow channel has a constant longitudinal section.

4. The connecting device according to claim 1, wherein the connection endpiece is of the Luer or Luer lock type, and comprises a first frusto-conical connection portion fluidically connected to the outlet orifice.

5. The connecting device according to claim 4, wherein the connection endpiece comprises a second connection portion interiorly threaded and surrounding the first frusto-conical connection portion.

6. The connecting device according to claim 1, wherein the connecting member comprises a plurality of receiving housings into each of which a medical treatment fluid administration tube is intended to be inserted and into each of which opens the proximal aperture of a flow channel.

7. The connecting device according to claim 6, wherein the receiving housings have an identical cross-section.

8. The connecting device according to claim 1, wherein the connecting member and the connection endpiece are transparent.

9. The connecting device according to claim 1, wherein the primary flow channel flares towards the internal chamber.

* * * * *